United States Patent
Bowman (10) Patent No.: US 11,439,416 B2
(45) Date of Patent: *Sep. 13, 2022

(54) OBSTRUCTION REMOVAL SYSTEM

(71) Applicant: MicroVention, Inc., Aliso Viejo, CA (US)

(72) Inventor: Heath Bowman, Trabuco Canyon, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 252 days.

This patent is subject to a terminal disclaimer.

(21) Appl. No.: 16/909,887

(22) Filed: Jun. 23, 2020

(65) Prior Publication Data

US 2020/0315644 A1    Oct. 8, 2020

Related U.S. Application Data

(60) Continuation of application No. 15/914,936, filed on Mar. 7, 2018, now Pat. No. 10,722,254, which is a continuation of application No. 14/938,732, filed on Nov. 11, 2015, now abandoned, which is a division of application No. 13/844,148, filed on Mar. 15, 2013, now Pat. No. 9,211,132.

(60) Provisional application No. 61/665,280, filed on Jun. 27, 2012.

(51) Int. Cl.
*A61B 17/22* (2006.01)
*A61B 17/221* (2006.01)

(52) U.S. Cl.
CPC ...... *A61B 17/22032* (2013.01); *A61B 17/221* (2013.01); *A61B 2017/22001* (2013.01); *A61B 2017/2212* (2013.01); *A61B 2017/22034* (2013.01)

(58) Field of Classification Search
CPC .......... A61B 2017/22034; A61B 2017/22035; A61B 2017/2212; A61B 2017/2215; A61B 2017/2217; A61B 17/22031; A61B 17/221; A61B 17/320725; A61B 17/22032; A61F 2/013; A61F 2/01; A61F 2/011; A61F 2/856; A61F 2/86; A61F 2/852; A61F 2002/016; A61F 2002/018; A61F 2002/823; A61F 2002/826
See application file for complete search history.

(56) References Cited

U.S. PATENT DOCUMENTS

| | | | |
|---|---|---|---|
| 6,066,149 A | 5/2000 | Samson et al. | |
| 6,254,571 B1 | 7/2001 | Hart | |
| 6,660,021 B1 | 12/2003 | Palmer et al. | |
| 6,702,834 B1 | 3/2004 | Boylan et al. | |
| 7,044,134 B2 | 5/2006 | Khairkhahan et al. | |
| 9,211,132 B2 | 12/2015 | Bowman | |

(Continued)

OTHER PUBLICATIONS

WIPO, U.S. International Search Authority, International Search Report and Written Opinion dated Oct. 16, 2013 in International Patent Application No. PCT/US2013/048322, 12 pages.

(Continued)

*Primary Examiner* — Majid Jamialahmadi
(74) *Attorney, Agent, or Firm* — Inskeep IP Group, Inc.

(57) ABSTRACT

An obstruction removal device is described, having one or more engaging members which can engage portions of the clot. The one or more engaging members have a collapsed, delivery state, and an expanded, deployed state.

20 Claims, 11 Drawing Sheets

(56) References Cited

U.S. PATENT DOCUMENTS

| | | |
|---|---|---|
| 2001/0031981 A1 | 10/2001 | Evans et al. |
| 2002/0002383 A1 | 1/2002 | Sepetka et al. |
| 2003/0120303 A1 | 6/2003 | Boyle et al. |
| 2005/0192620 A1 | 9/2005 | Cully et al. |
| 2005/0228417 A1 | 10/2005 | Teitelbaum et al. |
| 2006/0264974 A1 | 11/2006 | Khachin et al. |
| 2008/0119889 A1 | 5/2008 | Kusleika |
| 2008/0234722 A1 | 9/2008 | Bonnette et al. |
| 2008/0275488 A1 | 11/2008 | Fleming |
| 2009/0299403 A1 | 12/2009 | Chanduszko et al. |
| 2009/0306702 A1 | 12/2009 | Miloslavski et al. |
| 2010/0137892 A1 | 6/2010 | Krolik et al. |
| 2011/0082493 A1 | 4/2011 | Samson et al. |
| 2011/0125181 A1 | 5/2011 | Brady et al. |
| 2011/0213403 A1 | 9/2011 | Aboytes |
| 2013/0345739 A1* | 12/2013 | Brady .............. A61B 17/22031 606/200 |
| 2015/0223829 A1 | 8/2015 | Aboytes |

OTHER PUBLICATIONS

Canadian Intellectual Property Office, Office Action dated Jan. 7, 2020 in Canadian Patent Application No. 3,031,099, 4 pages.
Korean Patent Office, Office Action dated Jul. 19, 2019 with English translation in Korean Patent Application No. 10-2015-7001510, 14 pages.

* cited by examiner

OBSTRUCTION REMOVAL SYSTEM

RELATED APPLICATIONS

This application is a continuation of and claims priority to U.S. patent application Ser. No. 15/914,936 filed Mar. 7, 2018 entitled Obstruction Removal System, which is a continuation of and claims priority to U.S. patent application Ser. No. 14/938,732 filed Nov. 11, 2015 entitled Obstruction Removal System, which is a divisional of U.S. patent application Ser. No. 13/844,148 filed Mar. 15, 2013 entitled Obstruction Removal System, which claims benefit of and priority to U.S. Provisional Application Ser. No. 61/665,280 filed Jun. 27, 2012 entitled Obstruction Removal System, all of which are hereby incorporated herein by reference in their entireties.

BACKGROUND OF THE INVENTION

The present invention relates to devices used to capture and remove obstructions, such as clots or other matter, from the vascular system, and delivery of these devices to a target area within the vascular system.

The buildup of thrombus in vasculature can lead to formation of blood clots. The formation of clots can result in restricted blood supply to downstream areas of the vasculature. When these clots are located in the neurovascular system, these clots can lead to stroke. Recent technologies to deal with clot removal utilize devices designed to hold and capture the clot, followed by withdrawal of the device to physically remove these clots from the body. Several of these devices may fail to capture the clot in its entirety, or may promote clot fragmentation which may allow thrombus to dislodge and accumulate at another site, thus continuing the risk of stroke. In addition, several of these devices may promote endothelial denudation due to high friction between the device and the vessel wall. There is need for an obstruction removal device which reduces the likelihood of fragmented thrombus staying in the vasculature while maximizing the chance of mechanically capturing the clot, and limiting the risk of endothelial denudation.

SUMMARY OF THE INVENTION

In one embodiment according to the present invention, an obstruction removal device is described having a proximal axial core structure, a distal bumper structure and one or more engaging members mounted to the distal bumper structure.

In another embodiment according to the present invention, an obstruction removal device is described having a proximal structure, distal structure, and one or more connected engaging members between the two structures.

In another embodiment according to the present invention, an obstruction removal device is described having a proximal structure, distal structure, and one or more connected engaging members between the two structures, where at least one of the engaging members acts as a filter.

In one example of the previously described embodiments, the plural engaging members are substantially similar to each other.

In another example of the previously described embodiments, some of the plural engaging members are not substantially similar to the other engaging members.

In another example of the previously described embodiments, some of the plural engaging members actively engage the clot while one or more of the remaining engaging members do not engage the clot.

In one embodiment, the obstruction removal device is sheathed within a delivery device and delivered through a catheter.

In another embodiment, the obstruction removal device is delivered directly through the catheter.

In another embodiment, the device is used to retrieve foreign objects.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

For the purposes of the terminology described below, the terms clot, thrombus, embolus, and obstruction can be used synonymously. Though an obstruction removal device is described, the device can also be used to capture clot, thrombus, embolus, foreign bodies, or other matter. Engaging members on the device can engage clot, thrombus, embolus, foreign bodies, obstructions, or other matter.

Figure 1:
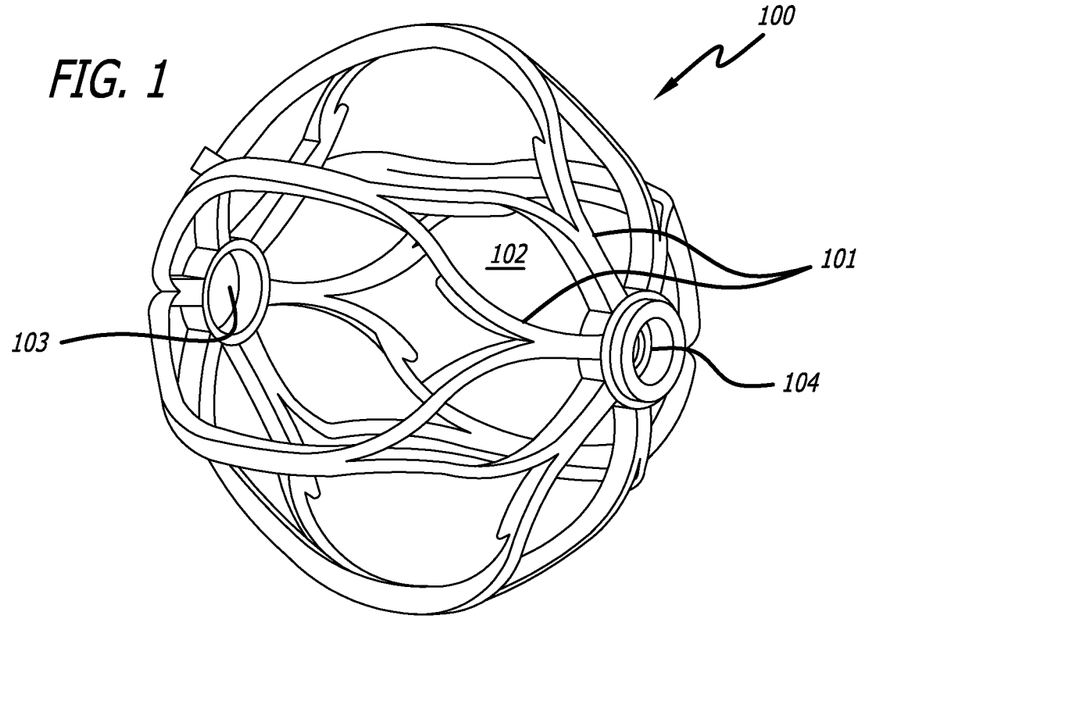
FIG. 1 is an engaging member used in an obstruction removal device.
Figure 2:
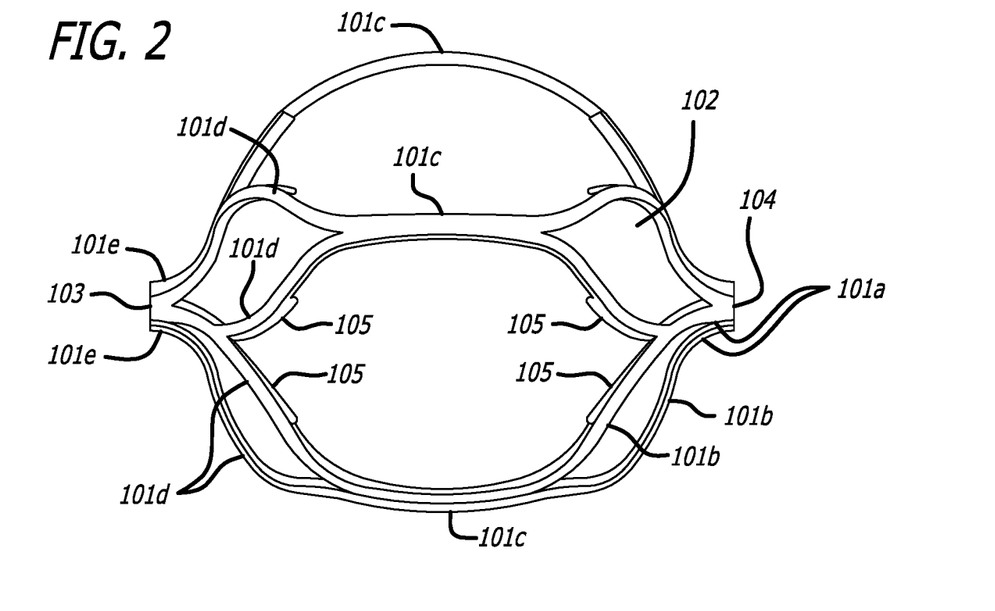
FIG. 2 is another view of the engaging member used in an obstruction removal device.

FIGS. 1 and 2 show an engaging member 100 used with the obstruction removal device of the present invention. One or more engaging members are used as part of an obstruction removal device in order to engage thrombus which can accumulate within a vascular system. General engaging member shapes can include, but are not limited to, round, oval, elliptical, hourglass, spherical, basket, stent, countered, rectangular, prismatic, cage. Each engaging member 100 has a number of struts 101 which define a number of cells, or openings 102, and a pair of opposing holes 103 and 104. For the sake of convention, hole 103 is a distal hole and hole 104 is a proximal hole.

Each engaging member may be uniquely configured with different struts, cells, cell sizes, materials, and/or shapes. The strut design can have a linear, wave, sinusoidal, or zig-zag pattern, or can have a non-symmetrical design (i.e. where struts on one side of the engaging member are not mirrored on the other side of said engaging member). The non-symmetrical strut design may help facilitate a rotational component on the member as it travels through a vessel, by shifting the center of gravity from the geometric center of the engaging member. This ease of rotation makes it easier for the engaging members, and therefore the obstruction removal device, to move more easily through the anatomy, especially after the clot has been engaged and the device is being pulled back through the vasculature. This ease of rotation can also limit the amount of damage to the vessel wall due to excessive contact friction by limiting the damage to a particular section of the wall. The engaging members may have either identical or unique designs on each end of the engaging member. This may be done by varying shape of the struts and/or cells, and/or varying the cell density of each end, thus—for example—allowing for large cell sizes on one end and smaller cell sizes on the opposing end. This variability may allow for different properties to allow for enhanced ability to engage the clot, or enhanced ability to track the obstruction removal device and deployed engaging members through the vessel.

FIG. 2 shows an engaging member 100 having a plurality of struts 101 having different thicknesses. More specifically, a plurality of end struts 101a branch out from the material defining proximal hole 104, and one or more of these struts 101a split to form struts 101b. Struts 101b are shown with features 105 protruding therefrom. Features 105 may be any interruption in the otherwise continuous surface of the strut 101. Non-limiting examples include barbs, bumps, protrusions, spikes, branches, nubs, and the like. The struts 101b are then shown as joining an adjacent struts 101b to form thicker struts 101c, which then split again to form additional struts 101d, also shown as having features 105. These struts 101d then join together again to form thicker struts 101e, which are connected to define distal hole 103. As such, it is seen that, in this particular embodiment, the struts interconnect to form a web of struts that span from the proximal hole 104 to the distal hole 103.

Another strut configuration could utilize a single strut pattern. An example includes a contiguous, helical strut configuration running between the proximal and distal ends of the engaging member, or running between a portion of the length spanning the proximal and distal ends of the engaging member.

Each engaging member has a collapsed configuration when sheathed within a delivery device, and takes on an expanded configuration as shown in FIGS. 1 and 2 when unsheathed. Each engaging member can be self-collapsible and self-expandable based on whether an external force is applied to constrain it (as would be the case when sheathed in a delivery device), or no constraining force is present (as would be the case when unsheathed).

The engaging member may be formed from nitinol, or a similar material, and may be laser cut to achieve the profile shape. Other materials and other cutting and/or machining processes would fit within the scope of the invention.

The distal and proximal holes, 103 and 104, on respective distal and proximal end of the engaging member, may facilitate placement of a common rod on which each engaging member sits, or they may fit separate connection pieces to connect multiple components of the obstruction removal device with the respective engaging members.

Figure 3:
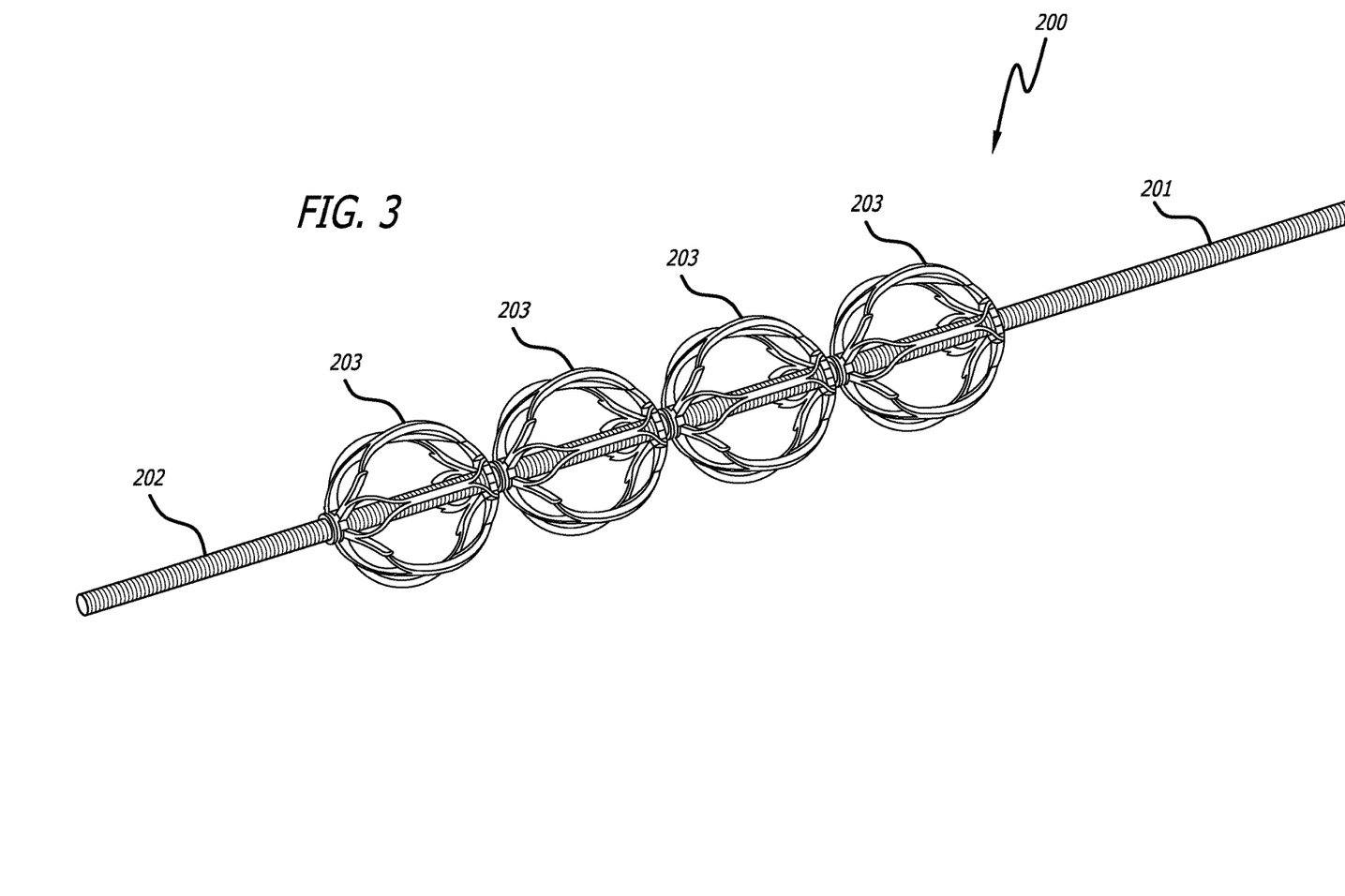
FIG. 3 is an obstruction removal device according to one embodiment of the present invention.

FIG. 3 illustrates an obstruction removal device 200 according to one embodiment of the present invention. The obstruction removal device comprises a proximal core structure 201 at one end of the device, a distal bumper structure 202 connected to the proximal core structure 201, and one or more engaging members 203 mounted to the distal bumper structure 202. In one example, the device is pushed and/or pulled from the core structure 201 end. A pusher may sit under the core structure, or the core structure itself may act as a pusher.

Core structure 201 may be made of a variety of materials, including, but not limited to, nitinol, stainless steel, cobalt chromium, or a polymeric material such as PTFE, Pebax, TPE, Engage, polyethylene, or other similar materials. Core structure configurations can include, but are not limited to, a coil, a braid, or a coil/braid combination.

The bumper structure 202 may be made of a radiopaque material, including, but not limited to, platinum, tantalum, palladium, or other similar material. A radiopaque material is preferred to make imaging of the device easier during the device insertion procedure, although non-radiopaque materials may also be used. The engaging members being mounted to the bumper structure, where the bumper structure is made of a radiopaque material, aids in imaging the device during the clot removal procedure. The engaging members may be mounted to the bumper structure in several ways. For example, the bumper structure may have a threaded outer profile, where the holes of the engaging members have a corresponding receiving structure to rotatably mate to the threaded bumper structure profile. Alternatively, the bumper structure may have a non-threaded outer configuration, and the engaging members may be affixed to the bumper structure by a heat treatment procedure, such as welding. Other mechanical means or other heat treatment procedures can also be used to affix the engaging members to bumper structure.

Figure 4:
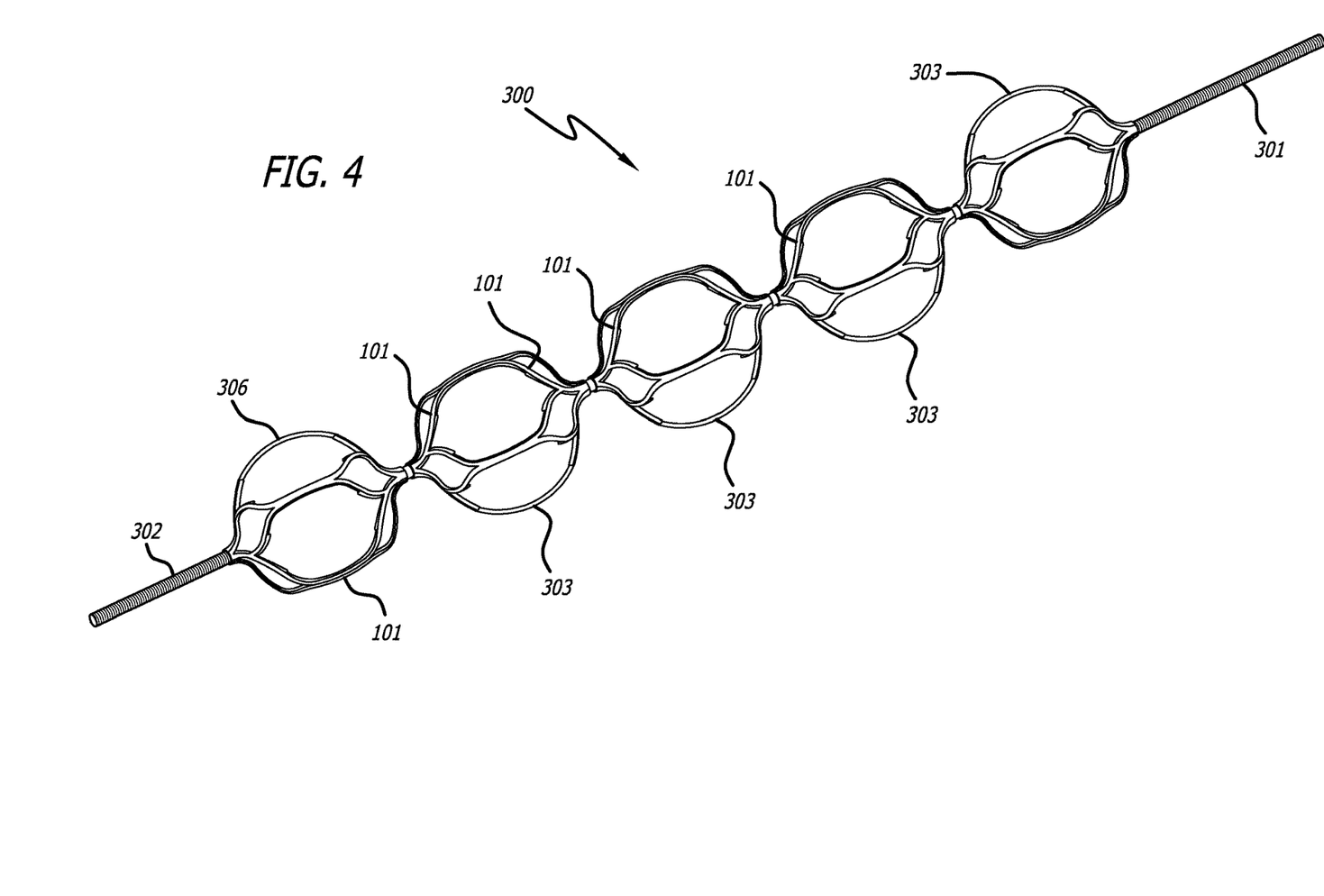
FIG. 4 is an obstruction removal device according to another embodiment of the present invention.

FIG. 4 illustrates an obstruction removal device 300 according to another embodiment of the present invention. The obstruction removal device 300 includes a proximal structure 301 connected to one or more engaging members 303. There may be a distal structure 302 attached to a distal-most engaging member (labeled as 306 for clarity, though it may be structurally the same or different as the other engaging members 303). The one or more engaging members 303 are connected to the proximal structure in such a way as to allow the one or more engaging members 303 to rotate independently of the proximal structure 301. The one or more engaging members 303 may be linked together to allow the engaging members 303 to rotate independently of each other as well, as discussed in more detail below. The obstruction removal device 300 is preferably pushed/pulled from one end of the proximal structure 301, thus the terms proximal portion structure and distal structure are used relative to the pushing/pulling end. Although five engaging members are illustrated in the figure, fewer or more engaging members can be used. Like all of the embodiments described herein, the engaging members 303 are constructed with one or more struts 101, as described above.

Figure 5:
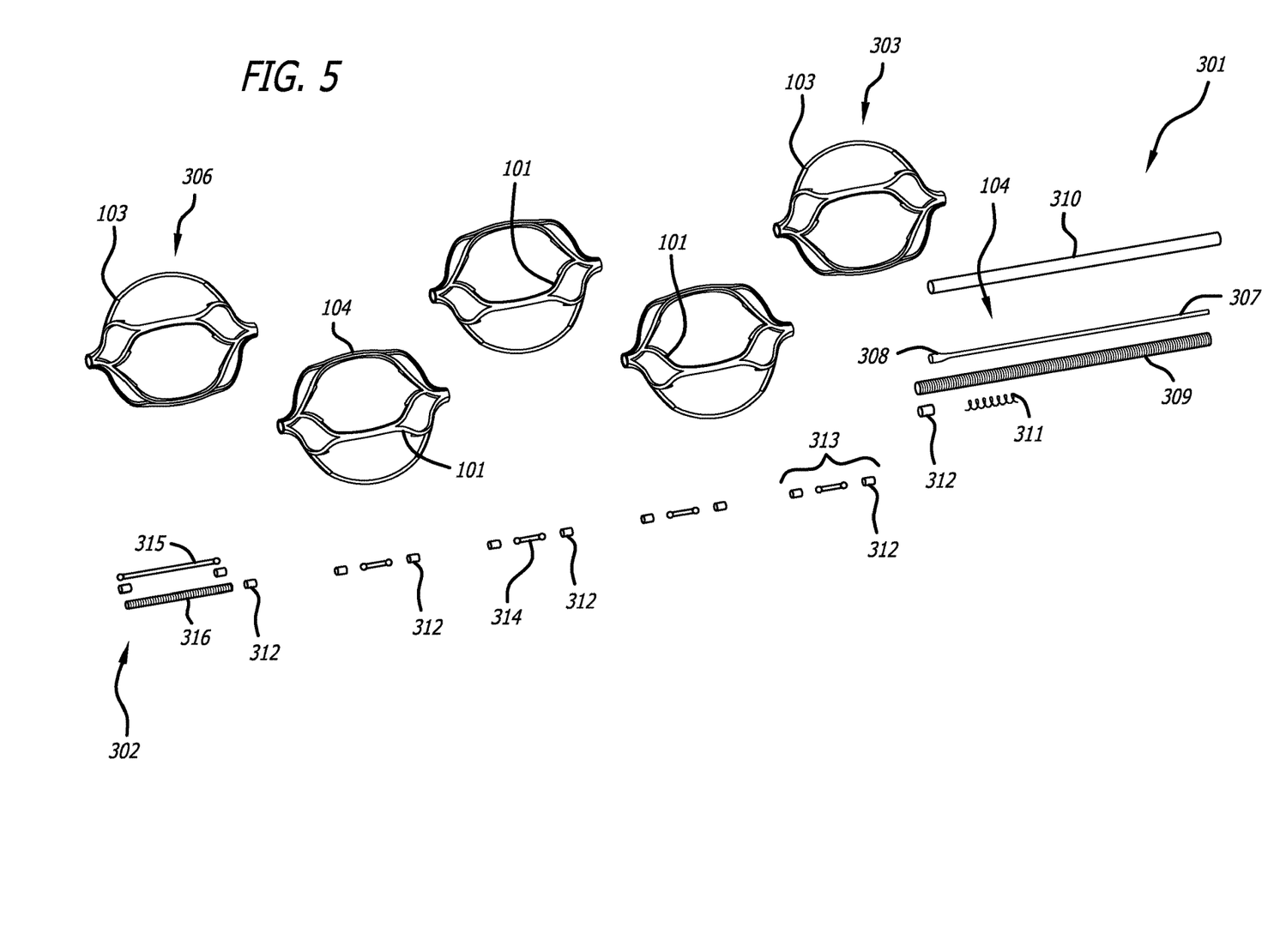
FIG. 5 is an exploded view of the obstruction removal device shown in FIG. 4.

FIG. 5 illustrates an exploded view of an embodiment of the obstruction removal device 300 of FIG. 4. The proximal structure 301 may include a core wire 307 which sits under a coil 309, which may sit under a tube 310. The core wire 307 includes a flared end 308. The core wire 307 may be made of nitinol, or a similar material, although other materials are within the scope of the invention. The coil 309 may be made of tantalum, or other radiopaque materials, although non-radiopaque materials may also be used. The tube 310 may be made of PET, or other polymeric material, although non-polymeric materials may be used as well. The proximal structure also includes another coil 311 which is preferably more gapped than coil 309, and can be made of a similar material. Coil 311 sits between core wire 307 and the over-coil 309, and helps center core wire 307 within coil 309. Proximal structure 301 is connected to a proximal engaging member 302, which can in turn be connected to another engaging member if more than one engaging member is used in the obstruction removal device.

The distal structure 302 includes a monofilament 315 which sits under a coil 316. Alternatively, multiple monofilaments can be bonded together to produce a monofilament structure 315. The monofilament 315 can be made of a stretch-resistant polymer such as Engage, although other materials may be used. The coil 316 may be made of tantalum, or other radiopaque materials, although non-radiopaque materials may also be used. Adhesive, preferably UV curable adhesive, 317 is used at both ends of the coil structure 316 in order to keep the monofilament 315 integral within the coil 316. In one example, the distal structure can act as a guidewire.

A distal structure 302 may be connected to the distal-most engaging member 306. This distal structure may be radiopaque in order to aid in imaging of the device during deployment. In the embodiment of FIG. 5, the coil of the distal structure 302 fits within the hole 103 of the distal-most engaging member 306, and a retaining piece 312 fits on the other end to keep the distal portion 302 integral with engaging member 306. The retaining piece is welded within the interior of the structure of hole 103. The engaging member 306 can still rotate. The retaining piece may be of a tubular construction, and may be made from nitinol, although similar materials can also be used. In order to aid in imaging, the retaining piece may be made from nitinol filled with a radiopaque material. Alternatively, the retaining piece may be coated with a radiopaque material to aid in imaging of the device during the procedure. Alternatively, the retaining piece may be made of a radiopaque material.

Figure 6:
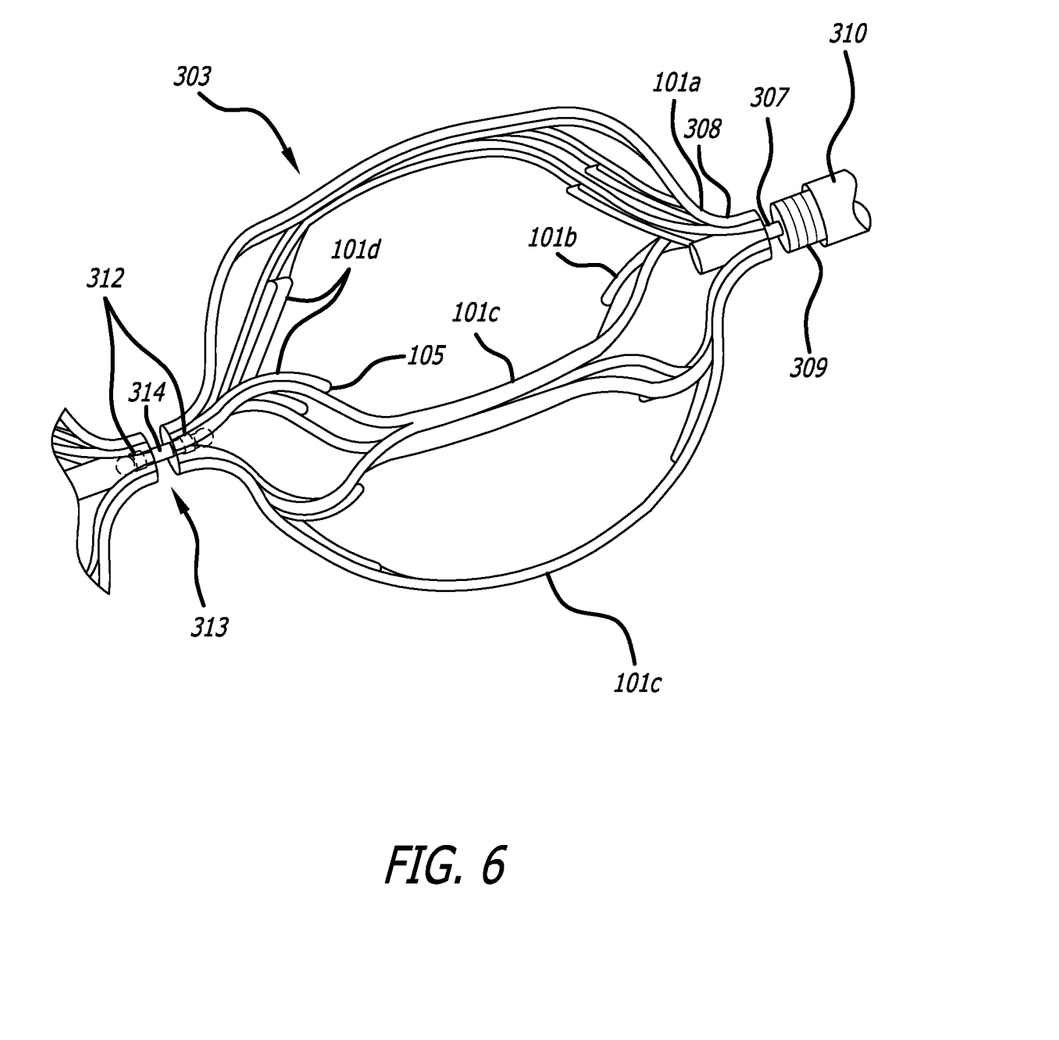
FIG. 6 is a magnified view of the proximal engaging member of the obstruction removal device of FIGS. 4 and 5.

The connection mechanism used to connect the engaging members together is shown in FIGS. 5 and 6. FIG. 6 illustrates the connection structure of engaging member 303, which is connected to the proximal structure 301 of the obstruction removal device.

The connection mechanism includes a link 313 with two flared ends 314, and retaining pieces 312. The link 313 may be made of stainless steel, although similar materials may be used. The flared ends extend within the opposing holes 103, 104 of the engaging members being connected, and the retaining piece 312 fits next to the flared end 314 to secure the link 313 within the hole of the engaging member. This connecting structure is used to connect the engaging members together, if more than one engaging member is used in the obstruction removal device. Retaining piece 312 is welded to the hole, and the link can rotate while secured within the hole of the engaging member. The engaging members may independently rotate.

Engaging member 303 is also connected to the proximal structure 301, as shown in FIGS. 5 and 6. The flared end 308 of the core wire sits past hole 104 of engaging member 303 and a retaining piece 312 sits over the core wire 307 to secure the proximal structure 301 to engaging member 303, where retaining piece 312 is welded within hole 104. A smaller, gapped coil 311 sits within the distal end of coil 309 and serves to help center the core wire 307 within the coil 309.

In one example, the connecting piece 313 is placed within the hole structure, and retaining piece 312 is welded into the hole over the connecting piece. The flared end 313 can subsequently be laser welded on the end of the connecting piece. In another example, the retaining piece 312 is welded into the hole and the connecting piece is placed within, and the flared end is laser welded. Although laser welding is specified, other similar heat treatment techniques can be utilized as well. This procedure can also be utilized at the end of core wire 307 to produce flared end 308, and to connect proximal-most engaging member 303 to the proximal portion 301 of the device. In one example, this procedure can be utilized at the end of the coil 316 when connecting the distal portion of the device to distal-most engaging member 306.

Each engaging member has a rotational component; this ability to rotate can aid in capturing the thrombus and navigating the vessel. This can also help limit the amount of endothelial denudation that may occur as the device is being pushed and/or pulled through the vessel, by helping to limit any excessive forces that build up due to excessive contact friction between the struts and the vessel wall. The engaging members may also be configured to have a more rounded, smoother profile (as illustrated in the figures) which would eliminate any sharp edges on the engaging members which may otherwise promote denudation due to high contact friction. Furthermore, due to the space between the engaging members, less material physically contacts the vessel than other designs which may utilize, for example, a longer one-piece clot engaging unit. Less material contacting the vessel will also serve to limit endothelial denudation during the clot removal procedure.

In one example, the proximal portion 301 of the obstruction removal device can include means to detach the engaging members from the obstruction removal device. The detachment means can be included on the portion of the proximal portion 301 contacting engaging member 303 (the proximal-most engaging member) and can include electrolytic, mechanical, thermal, or other means known in the art to induce severing and/or degradation of a linkage.

One or more of the engaging members may actively engage the clot, while other members can sit either distally beyond, or proximally before, the thrombus—depending on the size of the clot and the number of engaging members utilized on the device. Due to the potential variability in the individual shape and/or profile of each engaging member, as well as the number of engaging members used in the obstruction removal device compared to the size of the clot, one or more engaging members may sit distally past the clot and have a denser cell configuration to act as a filter for catching thrombus that may dislodge when capturing the clot utilizing the obstruction removal device. The engaging member(s) which act as a filter may have a mesh configuration; said mesh configuration can be throughout the whole engaging member or be located on one particular side of the engaging member, in order to maximize the chances of catching loose thrombus without the thrombus dislodging. In one example, the engaging member(s) which act as a filter has a denser cell configuration on the more-distal portion of said member in order to catch thrombus dislodged from interaction of the more proximal engaging members with the clot. This arrangement can be useful when the more proximal engaging members interact with the clot and portions of the clot macerate. The more distal engaging members with the filter configuration can catch macerated thrombus that otherwise might accumulate in the bloodstream. The engaging members which act as a filter may be formed from nitinol, stainless steel, or similar materials. Alternatively, they may be formed from laser cut polymers. Alternatively these engaging members acting as filters may have an inverted braid configuration, or other basket-type configurations, or other configurations known within the embolic protection device art. One or more of the engaging members may also be composed of a thrombogenic material, or may be coated with a thrombogenic material in order to aid in the clot retrieval procedure, by promoting adhesion between the engaging member and the thrombus. Alternatively, an anti-thrombogenic material can be used, or an anti-thrombogenic coasting can be used in order to help dissolve a portion of the clot that is in contact with the engaging members. This can be useful with, for instance, retrieval operations involving a large clot.

Figure 7:
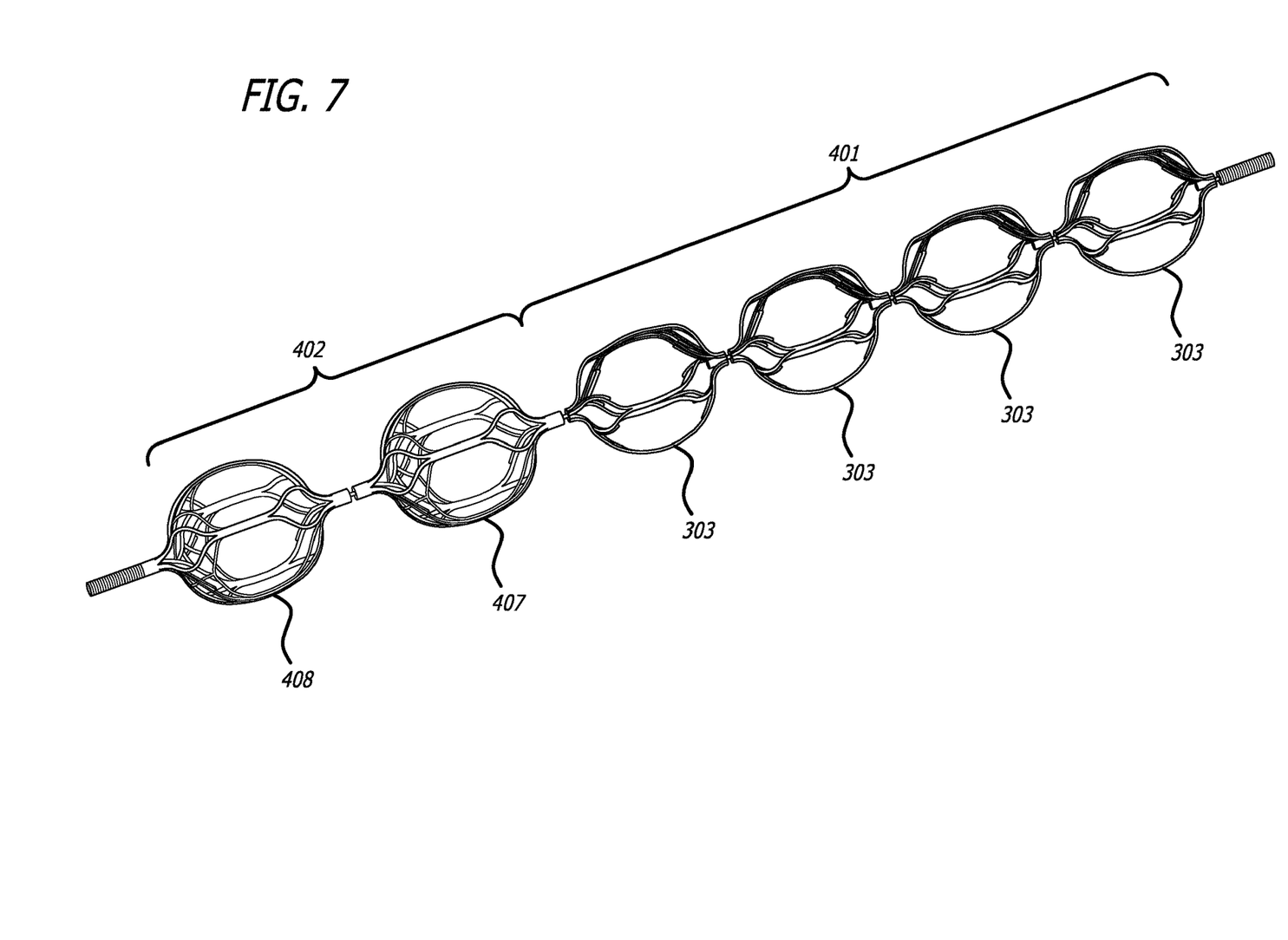
FIG. 7 is an obstruction removal device according to another embodiment of the present invention.
Figure 8:
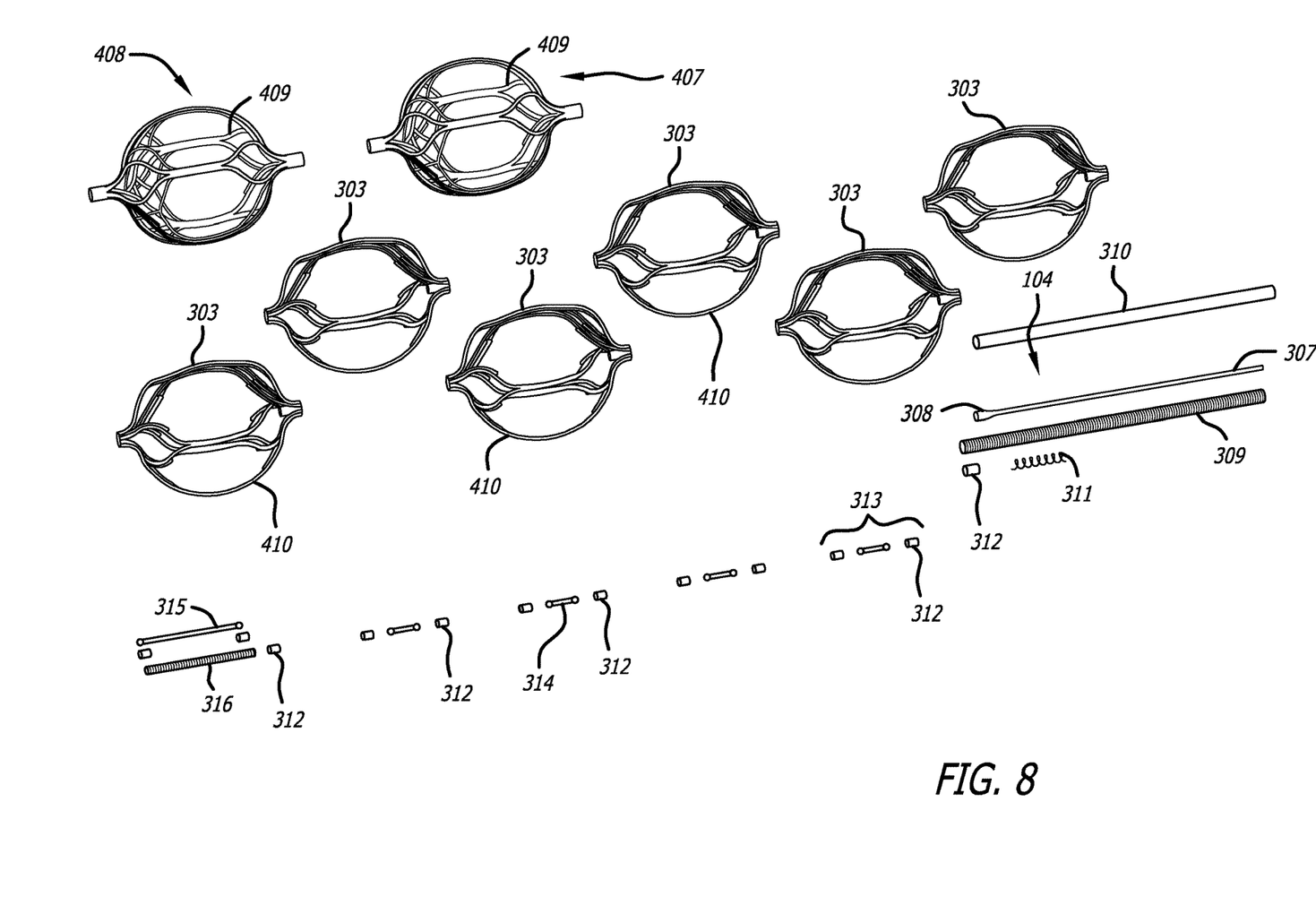
FIG. 8 is an exploded view of the obstruction removal device shown in FIG. 7.

FIGS. 7 and 8 illustrate another embodiment of the obstruction removal device utilizing one or more engaging members which act as a filter in order to catch thrombus that may become dislodged during the clot removal procedure. FIG. 7 illustrates the obstruction removal device, with a proximal portion 401 and distal portion 402. The proximal portion includes engaging members 303. The distal portion includes engaging members 407 and 408. The distal engaging members 407 and 408 have a denser cell configuration to act as a filter to trap dislodged thrombus which may shear off during the clot removal procedure, the clot removal procedure being generally described above. The denser cell configuration is due to an inner and outer structure used to form the engaging member, as illustrated in FIG. 8. As illustrated in FIG. 8, the two distal engaging members 407 and 408 are each composed of an inner structure 409 and outer structure 410, where the inner structure may nest within the outer structure. The inner structure 409 and outer structure 410 which comprise the distal engaging members 407 and 408 may be made from laser cut nitinol, or a similar material. The proximal portion 401 and distal portion 402 are configured the same as the embodiment presented in FIGS. 4-5, as are the linkages between each of the engaging members, although this filtering engaging member structure can be applied to any of the engaging members presented in any of the presented obstruction removal device embodiments.

Figure 9:
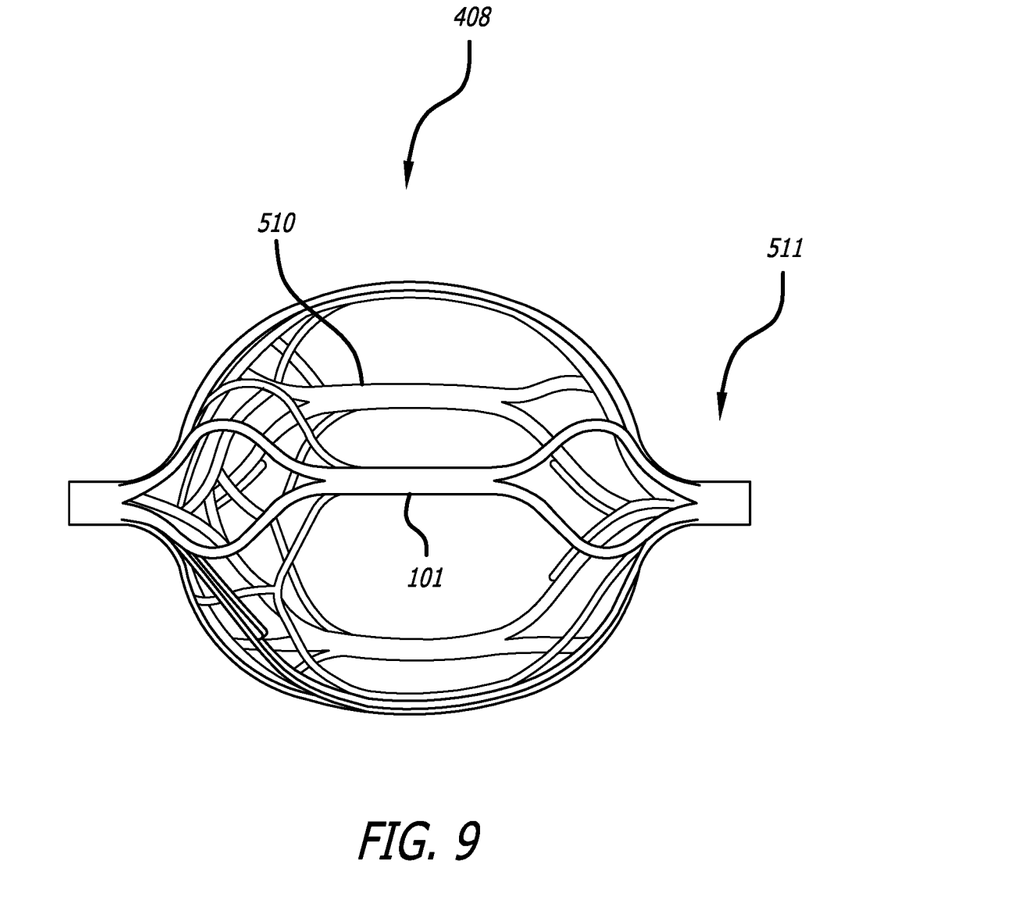
FIG. 9 is one of the distal engaging members used in the device shown in FIGS. 7 and 8.

The cell pattern may be slightly offset on the inner and outer structure in order to create a denser cell profile when the inner structure is nested within the outer structure. As shown in FIG. 9, the distal part 510 of the engaging member 408 has a denser cell profile than the proximal part 511 in order to catch dislocated thrombus which may escape during the clot removal procedure. This arrangement can be useful when the more proximal engaging members interact with the clot and portions of the clot macerate. The more distal engaging members with the filter configuration can catch macerated thrombus that otherwise might accumulate in the bloodstream. Although FIGS. 7 and 8 illustrate two engaging members having the inner and outer structure to act as a filter, more or fewer engaging members can have this filter structure.

In one embodiment for delivery of the device described in the previous embodiments, an obstruction removal device is sheathed within a delivery device, and the delivery device is delivered through a catheter. In one example, the delivery device can be a microcatheter. The delivery device is delivered to the site of the obstruction and then pulled back. Pulling back the delivery device unsheathes the obstruction removal device, such that the engaging members expand upon retraction of the delivery device. Alternatively, the obstruction removal device is pushed out of the delivery device, which subsequently allows the engaging members to expand. Depending on the number of engaging members on the obstruction removal device, the size of the clot, and the location of delivery relative to the obstruction, some members may sit distally past, and/or proximally before, the obstruction. The obstruction removal device may be maneuverable via the core wire. Once the obstruction removal device engages the obstruction, the delivery device can be withdrawn to a point just past the distal end of the catheter, and then the catheter can be withdrawn. Alternatively, the obstruction removal device can be withdrawn from the vasculature by withdrawing the delivery device into the catheter, and subsequently withdrawing the catheter, or withdrawing the delivery device and/or obstruction removal device through the catheter. Alternatively, the catheter can be withdrawn wholly to remove the delivery device and obstruction removal device. In another example, the delivery device can be a hypotube.

In an alternative embodiment, the device may be delivered directly through the catheter, without being sheathed in a delivery device.

Figure 10:
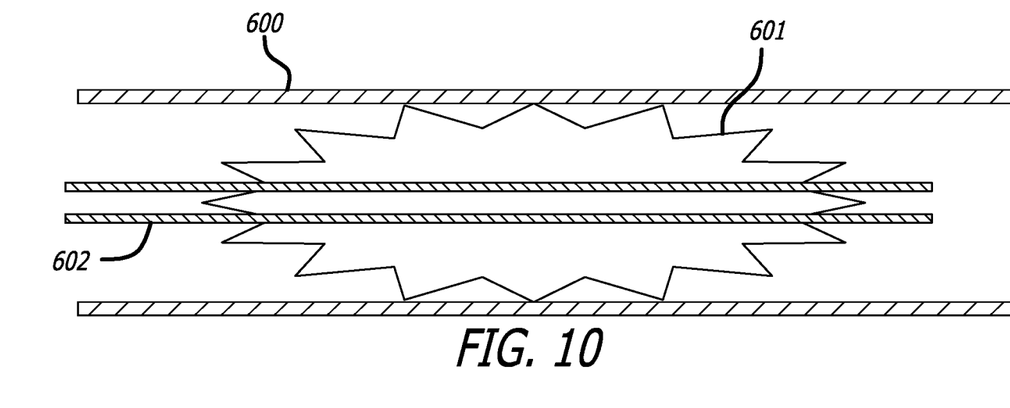
FIGS. 10-12 illustrate a method of deploying the obstruction removal device described in the previous embodiments.
Figure 11:
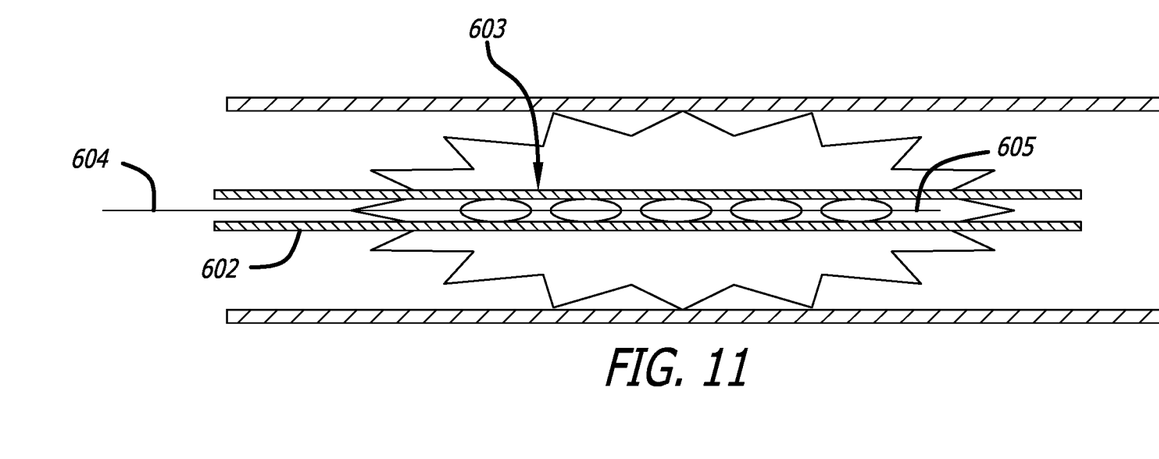
Figure 12:
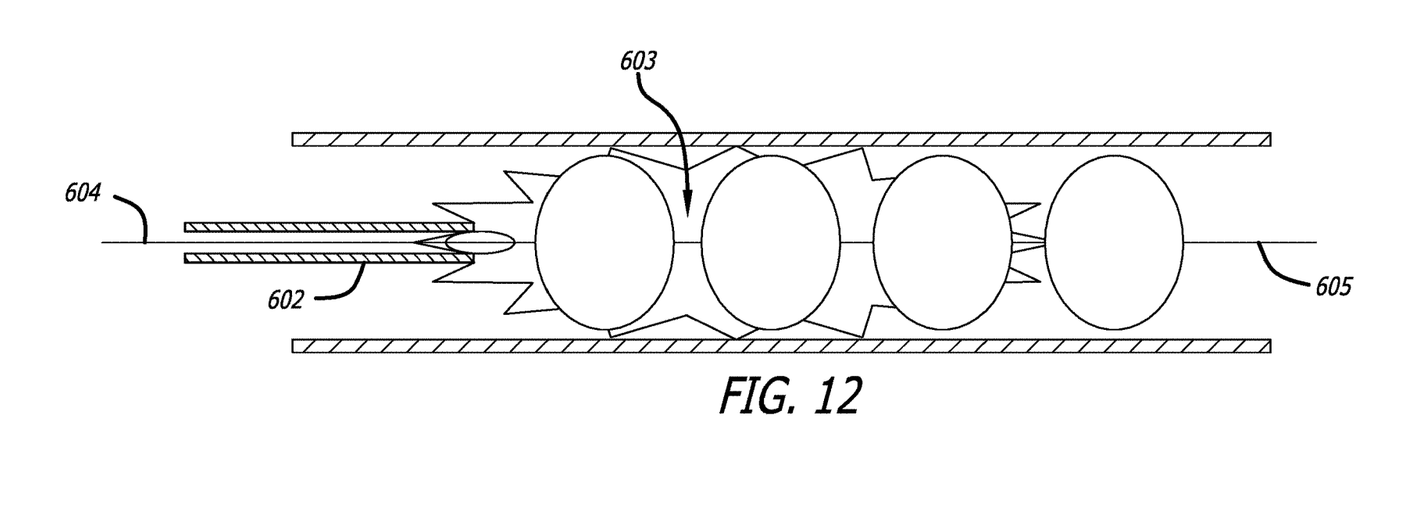

FIGS. 10-12 illustrate an example of a particular method for deploying the obstruction removal device. In this example, the delivery device 602 is delivered through the vasculature 600 to the site of the clot 601. The obstruction removal device 603 is pushed through the delivery device to the site of the clot. Although this particular example illustrates the obstruction removal device deployed in the middle of the clot, the device may be deployed within the clot, or in a location proximal or distal relative to the clot location. Some engaging members may sit distally past and/or proximally before the clot, depending on the size of the clot and the number of engaging members used on the obstruction removal device. Delivery device 602 is then retracted which allows the engaging members of the obstruction removal device to expand and interact with portions of the clot. The obstruction removal device 603 can be manipulated by the operator from the proximal portion 604 of the device. Once the obstruction removal device has secured the clot, the device can be withdrawn as described above. Aspiration may also be used to aid in the clot/obstruction removal procedure. FIGS. 10-12 illustrate a particular example for illustrative purposes. Other delivery methods are contemplated within the scope of the invention, such as pushing the obstruction removal device from the delivery device.

The engaging members may all be the same size, may all be different sizes, or may have some engaging members sized differently from others. In one example, the diameter range for spherically shaped engaging members may be between 1-12 millimeters. In another example a diameter range of 3-6 millimeters is used.

Figure 13:
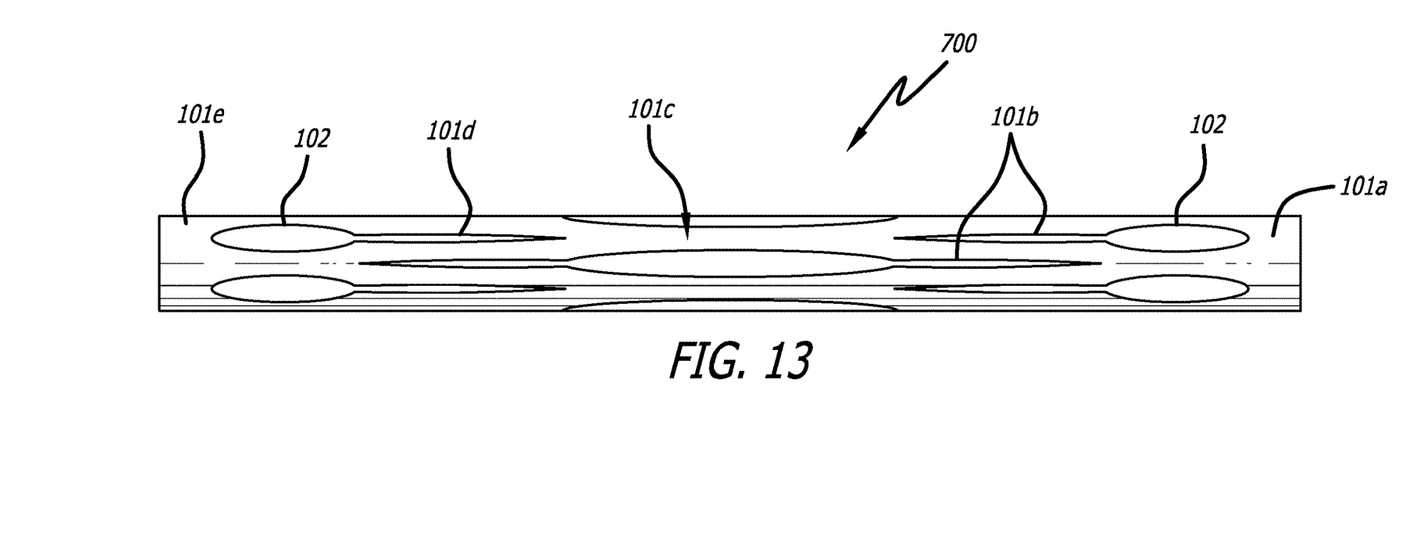
FIG. 13 illustrates a hypotube used to create an engaging member
Figure 14:
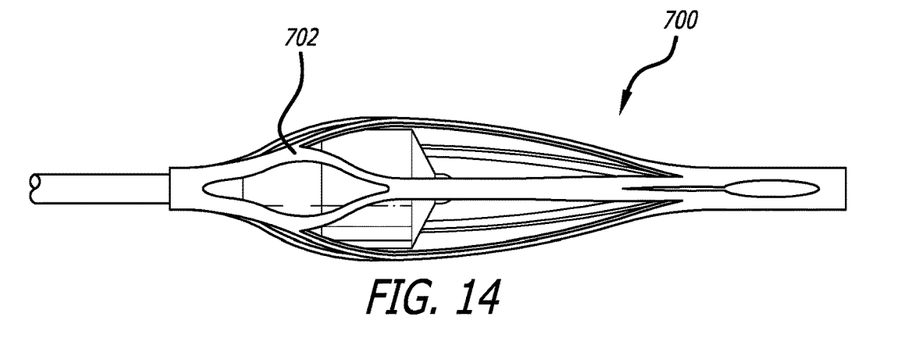
FIGS. 14-16 illustrate a process used to help set the final shape of an engaging member
Figure 15:
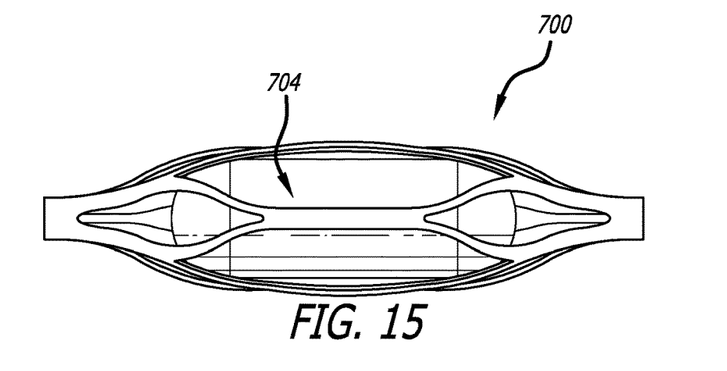
Figure 16:
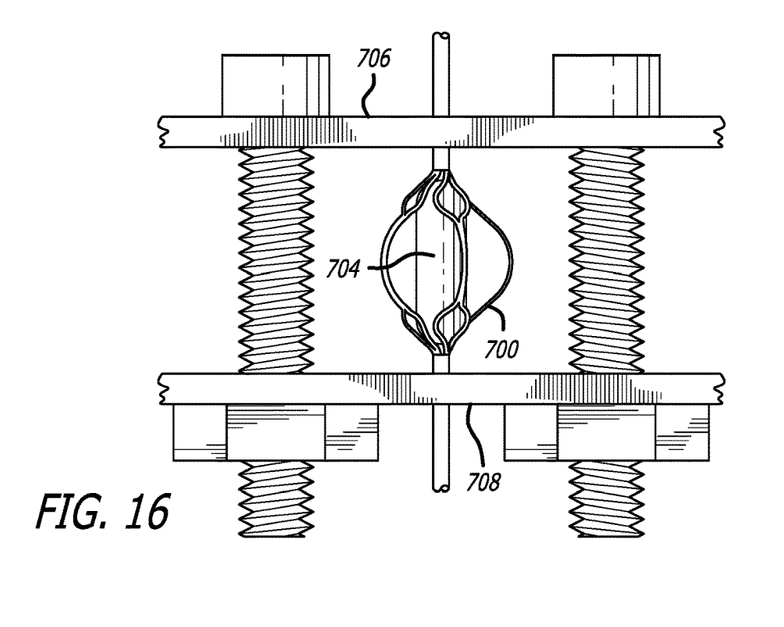

The engaging members are formed from a hypotube which is laser-cut into a particular pattern based on the shape of the struts 101 and cells 102. This hypotube 700 is shown in FIG. 13. The hypotube is heat treated, in one example the hypotube can be heat set at 530-550 degrees Celsius for 5 minutes. The hypotube is subsequently quenched in water to cool. An expansion plunger 702 is then inserted and used to expand a portion of the hypotube (see FIG. 14). The expanded hypotube is then heat-set to this expanded shape. In one example it is heat set at 530-550 degrees Celsius for 3 minutes. The expanded hypotube is subsequently quenched in water. Based on the size of the engaging member, the expansion plunger and subsequent heat treatment step can be used on multiple portions of the engaging member, where each section is heat set after expansion. An expansion pin 704 is subsequently inserted within the hypotube to help expand the walls of the hypotube (see FIG. 15). The expanded hypotube 700 is placed in a fixture. The fixture includes two plates 706, 708. Threaded rods connect the plates, and the plates have an external mounted nut. The nut can be tightened to compress the plates together in order to further expand the hypotube. Once the appropriate shape is set, the expanded hypotube can be heat treated (in one example, heat treated at 530-550 degrees Celsius for 5 minutes) and quenched to set the shape of the engaging member.

The engaging members are subsequently pickled, etched, and electropolished to set the final shape of the said members. The obstruction removal device is then assembled together with the one or more engaging members. Though the engaging members are heat-set and treated into an expanded shape, they still retain a high degree of shape memory due to factors such as material properties and strut thickness. Thus, the engaging members will adopt an expanded shape when not restrained (i.e. not sheathed in a delivery device) and will adopt a contracted shape similar to the initial hypotube shape when restrained (i.e. sheathed in a delivery device).

In an alternative embodiment, the device mentioned in the previous embodiments can be used to retrieve foreign objects, in addition to clots or other obstructions. Circumstances may arise where foreign objects, such as embolic coils normally used to fill an aneurysm, may break off or otherwise become detached within the vasculature. The device can be used to retrieve the foreign body utilizing a procedure similar to the procedure used during obstruction removal.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An obstruction removal device for capturing and removing obstructions from a vascular system comprising:
   a plurality of engaging members; and,
   a plurality of links in which each of the plurality of links connect one of the plurality of engaging members to an adjacent engaging member of the plurality of engaging members;
   wherein the plurality of links are configured such that at least one of the plurality of engaging members can rotate independently of another of the plurality of engaging members.

2. The obstruction removal device of claim 1, wherein each of the plurality of engaging members includes an opening which each of the plurality of links is positioned through.

3. The obstruction removal device of claim 1, wherein each of the plurality of engaging members includes two openings, each of the openings are positioned at a proximal end and a distal end of each of the plurality of engaging members.

4. The obstruction removal device of claim 1, further comprising a proximal structure connected to at least one of the plurality of engaging members.

5. The obstruction removal device of claim 4, wherein at least one of the plurality of engaging members can rotate independently of the proximal structure.

6. The obstruction removal device of claim 1, further comprising a distal structure connected to at least one of the plurality of engaging members.

7. The obstruction removal device of claim 6, wherein at least one of the plurality of engaging members can rotate independently of the distal structure.

8. An obstruction removal device for capturing and removing obstructions from a vascular system comprising:
   a plurality of engaging members that each have an opening; and,
   a plurality of links that are each positioned through the opening of at least one of the plurality of engaging members, each of the links connecting one of the plurality of engaging members to an adjacent engaging member of the plurality of engaging members,
   wherein at least one of the plurality of engaging members can rotate independently of another of the plurality of engaging members.

9. The obstruction removal device of claim 8, wherein each of the engaging members has an additional opening.

10. The obstruction removal device of claim 9, wherein the opening is a proximal end opening and the additional opening is a distal end opening.

11. The obstruction removal device of claim 8, wherein the plurality of links each include an elongate element and an enlarged end.

12. The obstruction removal device of claim 8, wherein the plurality of links each include an elongate element and two enlarged ends.

13. The obstruction removal device of claim 8, wherein each of the engaging members can rotate independently of each of the other of the plurality of engaging members.

14. The obstruction removal device of claim 8, wherein the plurality of links are configured such that at least one of the plurality of engaging members can rotate independently of another of the plurality of engaging members.

15. The obstruction removal device of claim 8, further comprising a proximal structure connected to at least one of the plurality of engaging members.

16. The obstruction removal device of claim 15, wherein at least one of the plurality of engaging members can rotate independently of the proximal structure.

17. The obstruction removal device of claim 8, further comprising a distal structure connected to at least one of the plurality of engaging members.

18. The obstruction removal device of claim 17, wherein at least one of the plurality of engaging members can rotate independently of the distal structure.

19. An obstruction removal device for capturing and removing obstructions from a vascular system comprising:
  three engaging members; and,
  two links, each of the links connecting one of the three engaging members to an adjacent engaging member of the three engaging members;
  wherein one of the three engaging members can rotate independently of two of the three engaging members.

20. The obstruction removal device of claim 19, further comprising a fourth engaging member and a third link.

* * * * *